United States Patent
Emerson et al.

(10) Patent No.: US 9,669,405 B2
(45) Date of Patent: Jun. 6, 2017

(54) STERILIZABLE PHOTOPOLYMER SERUM SEPARATOR

(71) Applicant: The Regents of the University of California, Oakland, CA (US)

(72) Inventors: Jane F. Emerson, Irvine, CA (US); Mohamad Al-Sheikhly, Potomac, MD (US)

(73) Assignee: The Regents Of The University of California, Oakland, CA (US)

( * ) Notice: Subject to any disclaimer, the term of this patent is extended or adjusted under 35 U.S.C. 154(b) by 1039 days.

(21) Appl. No.: 13/656,926

(22) Filed: Oct. 22, 2012

(65) Prior Publication Data
US 2014/0113795 A1    Apr. 24, 2014

(51) Int. Cl.
*B01L 3/00* (2006.01)
*G01N 33/49* (2006.01)

(52) U.S. Cl.
CPC ..... *B01L 3/50215* (2013.01); *B01L 2300/021* (2013.01); *B01L 2300/022* (2013.01); *B01L 2400/0677* (2013.01); *G01N 33/491* (2013.01)

(58) Field of Classification Search
CPC ........... B04B 5/0414; B04B 2005/0435; B01L 3/50215; B01L 2400/0677; B01L 2400/0683; B01L 2400/0409; B01L 2400/0475; G02N 33/491
USPC .............. 494/16, 20, 10; 422/131, 913, 918; 204/157.15
See application file for complete search history.

(56) References Cited

U.S. PATENT DOCUMENTS

| | | | |
|---|---|---|---|
| 3,647,070 A | 3/1972 | Adler | |
| 3,780,935 A | 12/1973 | Lukacs et al. | |
| 3,920,549 A | 11/1975 | Gigliello | |
| 3,920,557 A | 11/1975 | Ayres | |
| 3,976,579 A | 8/1976 | Bennett | |
| 4,050,451 A | 9/1977 | Columbus | |
| 4,052,320 A | 10/1977 | Jakubowicz | |
| 4,101,422 A | 7/1978 | Lamont et al. | |
| 4,190,535 A | 2/1980 | Luderer et al. | |
| 4,235,725 A | 11/1980 | Semersky | |
| 4,295,974 A | 10/1981 | Cornell | |
| 4,350,593 A * | 9/1982 | Kessler | 210/516 |
| 4,386,003 A | 5/1983 | Fiehler | |

(Continued)

FOREIGN PATENT DOCUMENTS

| | | |
|---|---|---|
| EP | 0350851 | 7/1989 |
| EP | 0350851 | 1/1990 |

(Continued)

*Primary Examiner* — Walter D Griffin
*Assistant Examiner* — Shuyi S Liu
(74) *Attorney, Agent, or Firm* — Fish & Tsang, LLP

(57) ABSTRACT

Sterilizable separator tubes and methods of utilization of same are presented. Methods include providing a separator tube containing a separator substance that can be polymerized to a desired hardness following sterilization using radical generating radiation. The separator substance is formulated to have a density between that of the average densities of separable fractions derived from a sample fluid such as blood, and to be flowable. Upon centrifugation of a separator tube containing a fluid sample, the separator substance forms a barrier between the fractions. The barrier subsequently hardens to form a solid barrier when triggered by a suitable energy source.

17 Claims, 1 Drawing Sheet

(56) References Cited

U.S. PATENT DOCUMENTS

| | | |
|---|---|---|
| 4,417,981 A | 11/1983 | Nugent |
| 4,457,782 A | 7/1984 | Honda et al. |
| 4,460,675 A | 7/1984 | Gruetzmacher |
| 4,569,764 A | 2/1986 | Satchell |
| 4,751,001 A | 6/1988 | Saunders |
| 4,770,779 A | 9/1988 | Ichikawa et al. |
| 4,816,168 A | 3/1989 | Carrol et al. |
| 4,844,818 A | 7/1989 | Smith |
| 4,867,887 A | 9/1989 | Smith |
| 4,894,315 A | 1/1990 | Feinberg |
| 4,946,601 A | 8/1990 | Fiehler |
| 4,994,393 A | 2/1991 | Pradhan et al. |
| 5,124,434 A | 6/1992 | O'Brien |
| 5,266,199 A | 11/1993 | Tsukagoshi et al. |
| 5,269,927 A | 12/1993 | Fiehler |
| 5,304,605 A | 4/1994 | Murakami et al. |
| 5,336,736 A | 8/1994 | Nakano |
| 5,354,838 A | 10/1994 | Murakami et al. |
| 5,454,958 A | 10/1995 | Fiehler |
| 5,489,386 A | 2/1996 | Saunders |
| 5,494,590 A | 2/1996 | Smith |
| 5,505,853 A | 4/1996 | Satake |
| 5,506,333 A | 4/1996 | O'Brien et al. |
| 5,510,237 A | 4/1996 | Isogawa et al. |
| 5,525,227 A | 6/1996 | Vogler |
| 5,527,843 A | 6/1996 | Murakmi et al. |
| 5,582,954 A | 12/1996 | Swatton |
| 5,663,285 A | 9/1997 | Rounds |
| 5,731,391 A | 3/1998 | O'Brien et al. |
| 5,776,357 A | 7/1998 | Okamoto et al. |
| 5,814,220 A | 9/1998 | Mikami et al. |
| 5,863,704 A | 1/1999 | Sakurai et al. |
| 5,888,824 A | 3/1999 | Isogawa et al. |
| 5,906,744 A | 5/1999 | Carroll et al. |
| 5,986,039 A | 11/1999 | O'Brien et al. |
| 6,072,022 A | 6/2000 | O'Brien et al. |
| 6,238,578 B1 | 5/2001 | Fiehler |
| 6,248,844 B1 | 6/2001 | Gates et al. |
| 6,280,622 B1 | 8/2001 | Goodrich et al. |
| 6,361,700 B2 | 3/2002 | Gates et al. |
| 6,595,940 B1 * | 7/2003 | D'Alessio ............ A61M 35/003 |
| | | 401/132 |
| 6,605,667 B1 * | 8/2003 | Badejo et al. ................ 524/753 |
| 6,979,307 B2 | 12/2005 | Baretta et al. |
| 6,989,226 B2 | 1/2006 | Araki |
| 7,090,970 B2 | 8/2006 | Anraku et al. |
| 7,211,037 B2 | 5/2007 | Briggs et al. |
| 7,673,758 B2 | 3/2010 | Emerson |
| 7,674,388 B2 * | 3/2010 | Emerson ............. B01L 3/50215 |
| | | 210/511 |
| 7,780,861 B2 | 8/2010 | Emerson |
| 7,932,302 B2 * | 4/2011 | Lu ......................... C08F 299/06 |
| | | 522/111 |
| 8,151,996 B2 | 4/2012 | Emerson |
| 8,206,638 B2 | 6/2012 | Emerson |
| 2002/0146677 A1 | 10/2002 | Augello et al. |
| 2006/0086675 A1 | 4/2006 | Purdum |
| 2006/0160025 A1 | 7/2006 | Lungu |
| 2006/0212020 A1 | 9/2006 | Rainen et al. |
| 2007/0003588 A1 | 1/2007 | Chinn et al. |
| 2007/0005024 A1 | 1/2007 | Weber et al. |
| 2007/0020629 A1 | 1/2007 | Ross et al. |
| 2007/0187341 A1 | 8/2007 | Emerson |
| 2009/0146099 A1 | 6/2009 | Anraku et al. |
| 2009/0301561 A1 * | 12/2009 | Wang et al. .................. 136/256 |
| 2010/0021522 A1 * | 1/2010 | Kuzma et al. ................ 424/423 |
| 2011/0263408 A1 | 10/2011 | Suto et al. |

FOREIGN PATENT DOCUMENTS

| | | |
|---|---|---|
| EP | 0375566 | 6/1990 |
| EP | 0520185 | 12/1992 |
| EP | 0384331 | 6/1994 |
| EP | 0705882 | 9/1995 |
| EP | 0705882 | 4/1996 |
| EP | 00705882 | 4/1996 |
| EP | 0744026 | 11/1996 |
| EP | 0766973 | 4/1997 |
| EP | 00928301 | 7/1999 |
| EP | 0928301 | 7/1999 |
| JP | H08187236 A | 7/1996 |
| KR | 1020050030337 | 3/2005 |
| KR | 1020050115235 | 12/2005 |
| KR | 10-2006-0073446 | 6/2006 |
| KR | 10-2006-0108149 | 10/2006 |
| WO | 99/64931 | 12/1999 |
| WO | 09964931 | 12/1999 |
| WO | WO2005011495 | 2/2005 |
| WO | 2005-063225 | 7/2005 |
| WO | WO2007139018 | 12/2007 |
| WO | 2009/085355 | 7/2009 |
| WO | 2010077534 | 7/2010 |
| WO | 2011105253 | 9/2011 |
| WO | WO 2014029062 A1 * | 2/2014 ............ C09J 175/16 |

\* cited by examiner

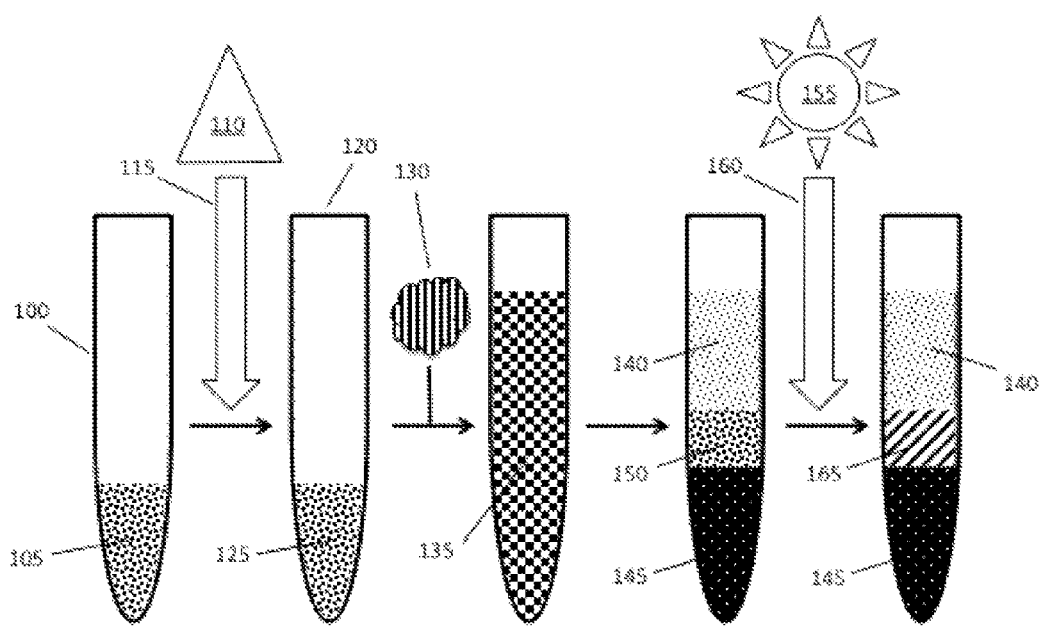

STERILIZABLE PHOTOPOLYMER SERUM SEPARATOR

FIELD OF THE INVENTION

The field of the invention is fluid separation, and especially to blood serum separation using a composition that forms a barrier between the separated phases.

BACKGROUND

Analysis of blood samples often requires separation of whole blood into a serum or plasma fraction and a cell-containing fraction prior to assay. Typically this is performed by collecting a blood sample in a blood collection or separation tube. Ideally such a blood collection or separation tube should be sterilizable in order to avoid microbial contamination of the sample and to simplify long term storage. Since blood collection/separation tubes are produced in large numbers and are provided as sealed containers with reduced internal pressure (in order to facilitate blood collection) such sterilization is typically carried out using ionizing radiation, such as gamma or e-beam irradiation, or other methods that permit sterilization of the contents of closed containers. Following sample collection, the blood collection or separation tube is transferred to a centrifuge where it is spun at relatively high speed. This application of centripetal force generates a density gradient within the tube, with heavier elements of the blood sample (for example, blood cells) collecting in the bottom of the tube as a dense phase or fraction while lighter elements (for example, serum or plasma) collect towards the top as a light phase or fraction. Following removal from the centrifuge the separation tube may be moved to an analyzer or, alternatively, placed in storage.

Unfortunately, once blood is separated in this manner these phases or fractions can remix through diffusion, agitation, disturbance during sample extraction or removal from storage, or other undesirable interactions. The situation is exacerbated by rupture of cells within the dense cell-containing fraction on storage. This can lead to contamination between the fractions, which can adversely impact assay performance. Ideally, therefore, blood fractions should remain isolated from one another following separation to ensure that no contamination occurs prior to or during analysis.

Systems that isolate the whole blood fractions generally include a separator substance or device that has a density intermediate between that of the cell-containing fraction and the serum/plasma fraction of whole blood, which allows the separator substance or device to localize between these fractions spontaneously during centrifugation. This allows the separator substance or device to act as a physical barrier to mixing due diffusion, agitation, and other disturbances. A suitable density is typically between 1.01 $g/cm^3$ and 1.09 $g/cm^3$. When whole blood is added to a collection or separator tube containing a separator substance and the tube is centrifuged, the separator substance migrates to the interface between the fractions thereby isolating the two fractions from each other. An exemplary collection tube that utilizes a flowable gel as a separator substance in the fractionation of whole blood can be found in U.S. Pat. No. 4,946,601 (to Fiehler). Another example of a separator substance that is flowable in the preparation of fractions from whole blood can be found in U.S. Pat. No. 6,248,844 and U.S. Pat. No. 6,361,700 (to Gates et al). In these patents the separator substance is a polyester that is cured to achieve a desired viscosity. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Although providing a flowable substance allows for separating the fractions of whole blood, flowable substances have several disadvantages. A flowable substance still remains flowable after centrifugation is complete. A result of this physical instability is that there remains a risk of contamination between the fractions of the sample unless proper care is taken to keep the blood collection tube suitably still and protected from agitation. While it is possible to use a gel-based separation substance that is formulated or configured with a viscosity that is high enough to provide a sufficiently solid barrier to overcome these disadvantages, such a separation substance may no longer be suitably flowable with whole blood and therefore require prohibitively long centrifuge times. Short centrifuge times are important for maintaining high throughput in the clinical laboratory and may be critical in life or death situations where a blood analysis result is required quickly.

One approach to resolving this issue is to utilize a thixotropic gel as a separator substance in a blood collection tube. Thixotropic gels have viscosities that change depending upon the shear stress applied to them. For example, a thixotropic gel may have a low viscosity that allows it to flow relatively easily when under the shear force applied by a centrifuge, but may have a high viscosity that makes it resistant to flow when it is at rest following centrifugation. U.S. Pat. No. 4,818,418 (to Saunders), for example, discusses the use of thixotropic gels in blood collection tubes. The problem with thixotropic gels, however, is that the relatively viscous gel that localizes between the blood fractions remains at least somewhat flowable and does not form a sufficiently solid separation barrier. As a result, when a sample is extracted from the tube with a pipette or similar device it is possible for such a separation substance to contaminate, foul, or plug the pipette if it contacts such a separation barrier. Moreover, it is also not uncommon that pieces of the separation substance float in the upper phase and cumulatively plug probes of an analyzer. While most analyzers have depth sensors, such sensors do not solve the problem of floating separator substances, and also waste plasma as use of such sensors require clearance above the separator substances.

An alternative approach taken by some medical device manufactures is to place a moveable, solid barrier substance or device within the blood collection tube. Examples of such solid substances include the intermediate density polymers found in U.S. Pat. No. 3,647,070 (to Adler) where polymer spheres or granules of a specified density aggregate to form a barrier layer. Similarly, U.S. Pat. No. 5,266,199 (to Tsukagoshi et al) describes an elastic tube and ball valve assembly that controls separation of the serum from the cell-containing phase. Such physical barriers, however, necessarily include gaps between the individual components and therefore only provide a partial seal between the separated blood fractions. Moreover, a further disadvantage to a movable barrier is that such containers must be filled adequately and allow for differences in relative proportions of fractions.

Yet another approach to providing a solid barrier between fractions in a blood collection/separator tube is disclosed in U.S. Pat. No. 7,673,758, U.S. Pat. No. 7,674,388, U.S. Pat.

No. 7,780,861, U.S. Pat. No. 8,151,996, and U.S. Pat. No. 8,206,638 (to Emerson). These disclose the use of a thixotropic gel within a blood collection or separator tube that has a low viscosity during centrifugation, allowing it to flow relatively freely and localize between the dense cell-containing fraction and the relatively low density serum/plasma fraction during centrifugation. The thixotropic gel includes a polymer with reactive groups that are capable of forming chemical crosslinks and a polymerization initiator. Activation of the initiator following centrifugation causes the reactive groups of the polymer to form covalent bonds that crosslink polymer molecules within the gel. This crosslinking forms a solid, impermeable polymer barrier between the cell-containing and serum/plasma blood fractions. The problem of adequately sterilizing a blood collection or separator tube containing such a composition, however, is not addressed.

These and other solutions for whole blood separation lack the necessary features to ensure that both the separated fractions of whole blood are effectively protected against contamination due to microbial growth and undesirable interactions between sample fractions/phases while supporting short centrifugation times. Thus, there is still a need for liquid separation technologies in which the separation barrier is solidified after centrifugation and that allow for effective and economical sterilization of devices incorporating them.

SUMMARY OF THE INVENTION

The inventive subject matter provides apparatus, systems and methods in which one can provide a stable, and substantially solid separation barrier between phases of a sample in order to reduce contamination between the phases. The separation barrier is formed within a separator tube that is sterilizable. In one embodiment of the inventive concept this may be accomplished by providing a separator composition within the separator tube, where the separator composition includes one or more polymerizable compounds, a radical scavenger, and a polymerization initiator (such as a radical photoinitiator). The radical scavenger's composition and concentration is such that exposure of the separator tube (or a portion thereof) to ionizing radiation at doses sufficient to sterilize the separator tube do not result in polymerization of the polymerizable compound(s). Suitable radical scavengers may include antioxidants, radioprotectives, free radical inhibitors, stabilizing free radical inhibitors, free radical interceptors, and free radical scavengers. Surprisingly, following sterilization treatment with ionizing radiation a substantially solid crosslinked composition may still be formed from the polymerizable compound(s) (such as an aliphatic urethane diacrylates and/or an aliphatic acrylate) on irradiation of the separator tube (or a portion thereof) by radical polymerization initiated by a suitable energy source, such as UV and/or visible light. This crosslinked composition can act as an impermeable separation barrier within the separator tube. In some embodiments of the inventive concept this separation barrier is substantially complete within about 10 minutes of the initiation of irradiation of the separator tube (or a portion thereof) with a suitable energy source.

Another embodiment of the inventive concept can be a method for separating phases of a sample within a separator tube. In such a method a separator tube is provided that includes a separator composition that is subject to radical polymerization to form a substantially crosslinked composition. This separator tube may be irradiated with ionizing radiation, thereby generating free radicals in amounts sufficient to effectively sterilize the separator tube, for example by exposure to gamma irradiation or e-beam irradiation at a dosage of at about 15 kGy or more. A portion of these free radicals are scavenged by a free radical scavenger, which, surprisingly, can prevent polymerization from occurring to a substantial degree as a result of this sterilizing irradiation while still permitting subsequent radical polymerization. Suitable free radical scavengers for this purpose include antioxidants, radioprotectives, free radical inhibitors, free radical interceptors, free radical scavengers, and stabilizing free radical scavengers. Such free radical scavengers are present in a concentration effective for preventing polymerization during sterilization with ionizing radiation, for example from about 2 mM to about 8 mM. Following sterilization a sample may be added to the separator tube and mixed with the separator composition, followed by centrifugation of the separator tube to separate the sample into low density and high density phases. In this process the density of the separator composition may be selected such that the separator composition localizes between these low density and high density sample phases. Subsequent irradiation of the sample tube with, for example, UV and/or visible light may then be used to initiate radical polymerization of polymerizable compounds (such aliphatic urethane diacrylates and/or aliphatic acrylates) of the separator composition to form a substantially solid, cross-linked composition that can act as an effective barrier between the phases of the sample. Formation of this cross-linked composition may be substantially complete within about 10 minutes of UV and/or visible light irradiation. In some embodiments of the inventive concept irradiation of the separator tube with UV and/or visible light may take place within a centrifuge.

In yet another embodiment of the inventive concept, a density filler may be utilized to adjust the density of a separator composition for use in a separator tube. Incorporation of the density filler may be accomplished by blending one or more polymerizable compound(s), a radical scavenger, and a radical photoinitiator to form a base mixture. A density filler can then be blended into the base mixture, forming a density-adjusted separator composition that may be filled into a separator tube. The separator tube may be exposed to a radical generating energy source (for example, gamma radiation or e-beam radiation) for a sufficient time that this irradiation sterilizes the separator composition and the separator tube. In such an embodiment, the radical scavenger is present in an amount sufficient to prevent polymerization of the polymerizable compound(s) on sterilizing irradiation, but to permit polymerization of the polymerizable compound(s) on activation of the radical photoinitiator. In some embodiments of the inventive concept substantial polymerization of the polymerizable compound(s) occurs within about 10 minutes or less of activation of the photoinitiator. Such activation may be performed by irradiation of the photoinitiator with a UV and/or visible light source. In other embodiments of the inventive concept additional processing steps such as incubation of the base mixture for a predetermined period, further mixing of the base mixture, and/or clarification of the base mixture prior to blending in the density filler are contemplated. Additionally, the density-adjusted separator composition may be incubated at an elevated temperature (for example, from 40° C. to 90° C.) following irradiation.

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWING

The drawing FIGURE is a schematic of an embodiment of the inventive device, showing sterilization of a separator tube, followed by sample addition, phase separation, and subsequent formation of a solid separation barrier between the separated phases.

DETAILED DESCRIPTION

The inventive subject matter provides apparatus, systems and methods in which one can provide a stable, and substantially solid separation barrier between phases of a sample in order to reduce contamination between the phases. The separation barrier is formed within a separator tube that is sterilizable. It should be noted that while the following description is drawn to a separator tube and/or blood collection tube, various alternative configurations are also deemed suitable and may employ various separation devices including syringes, vials, bottles, flasks, biurets, tubes, columns, funnels, or any other type of sample containment or separation device suitable for sample separation, operating individually or collectively. One should appreciate that a sample containment or separation device has a wall suitable for sample containment and should be at least partially permeable or transparent to the energy emitted by energy sources utilized in embodiments of the inventive concept. It should also be recognized that the term fluid as utilized throughout the application may refer to a liquid, gas, suspension, semisolid, and/or other flowable substance, either alone or in combination.

One should appreciate that the disclosed devices and methods provide many advantageous technical effects including provision of a solid, impermeable barrier between separated phases of a sample (for example, a fluid sample) in a sterilizable separator tube, thereby preventing contamination due to growth of microorganisms and to mixing between the phases as a result of diffusion, disturbance of the separator tube, freeze/thaw, etc. In addition, such a solid, impermeable barrier, being non-flowable, does not contaminate pipetting devices that come into contact with it.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In one embodiment of the inventive concept a substantially solid (e.g., at least 1 on the Shore 00 hardness scale) barrier may be provided between separated fluid fractions/phases by supplying a sterilizable separator tube which contains a separator composition, such that on addition of a sample to the separator tube the separator composition may be mixed and subsequently localized between fractions (or phases) of the sample on separation of the fractions. Following this separation the separator composition may be treated to form a substantially solid barrier. In some embodiments of the inventive concept this may be accomplished by providing a separator composition in the form of a flowable gel within a separator tube. The density of this gel is selected to be intermediate between the densities of the fluid phases or fractions that are to be separated. For example, if the fluid to be separated is blood the density of the gel could range from 1.01 to 1.09 g/cm$^3$. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary. In a preferred embodiment of the inventive concept the gel has a density of about 1.04 g/cm$^3$. In some embodiments of the inventive concept the separator composition is a thixotropic gel.

In further contemplated embodiments of the inventive concept a separator composition may include one or more polymerizable compounds (which support crosslinking to form a substantially solid barrier to contamination between separated phases or fractions), one or more radical scavengers, and one or more polymerization initiators. In such embodiments of the inventive concept the polymerizable compounds may have two or more (i.e. a plurality) reactive groups, while others may have a single reactive group. In a preferred embodiment of the inventive concept the separator compound includes polymerizable compounds with two or more reactive groups and polymerizable compounds with a single reactive group. This advantageously permits control over the degree of polymerization, and hence physical and chemical properties of the resulting polymerized materials. For example, increasing the percentage of a polymerizable compound with a single reactive group in such a mixture may allow the generation of polymerized materials with improved adhesion to surrounding materials, such as the interior wall of a separation tube. While it is generally preferred that the separator tubes include an oligomeric urethane acrylate and/or an aliphatic acrylate, it should be noted that the exact nature of the polymerizable material is not limiting to the inventive subject matter, and that numerous alternative polymerizable materials and polymers are also suitable. Indeed, all known polymers suitable for blood separation are deemed appropriate for use herein, including silicon oil, polyamides, olefinic polymers, polyacrylates, polyesters and copolymers thereof, polysilanes, and polyisoprenes. Suitable polymerizable materials are described in U.S. Pat. No. 7,673,758, U.S. Pat. No. 7,674,388, U.S. Pat. No. 7,780,861, U.S. Pat. No. 7,971,730, U.S. Pat. No. 8,151,996, and U.S. Pat. No. 8,206,638, which are incorporated herein by reference. In a preferred embodiment the separator composition includes EBECRYL 230™ and EBECRYL 113™ (Cytec Industries, Woodland Park, N.J. USA 07424).

As noted above, the separation composition may include one or more polymerization initiator(s). Such a polymerization initiator may be utilized to initiate polymerization of a polymerizable compound of the separator composition in a controllable manner, for example on the application of a suitable energy source. In a preferred embodiment of the inventive concept the polymerization initiator is a photoinitiator. Such a photoinitiator may be activated to generate free radicals that support polymerization of suitable polymerizable compounds on exposure to UV and/or visible light. Exemplary photoinitiators include, but are not limited to, benzoin ethers, benzyl ketals, alpha-dialkoxy-acetophenones, alpha-hydroxy-alkylphenones, alpha-amino-alkylphenones, acyl-phosphine oxides, benzophenones, benzoamines, thioxanthones, thioamines, and titanocenes. In a preferred embodiment the radical initiator is ADDITOL™ (Cytec Industries, Woodland Park, N.J. USA 07424). In some embodiments of the inventive concept activation of a photoinitiator may be performed by energizing a suitable source of UV and/or visible light. Such light sources include, but are not limited to, a fluorescent lamp, arc light, mercury vapor light source, xenon light source, LED, laser, and combinations thereof. In some embodiments of the inventive concept a suitable energy source for use with a photoinitiator may be incorporated into equipment used for storage, handling, and/or processing of a separator tube. For example, a suitable light source may be incorporated into a centrifuge utilized for separation, a refrigerator or incubator utilized for storage one or more separator tube(s) containing sample, a rack utilized for storage one or more separator tube(s) containing sample, and/or a transport/processing line of a laboratory management system and/or analytical system. Alternatively, a suitable light source may be incorporated into a handheld unit used for manual exposure of the separator tube.

In addition to one or more polymerizable compound(s) and polymerization initiator(s), a separation compound of the inventive concept may include one or more radical scavengers. Examples of suitable radical scavengers include (but are not limited to) antioxidants, radioprotectives, free radical inhibitors, stabilizing free radical inhibitors, free radical interceptors, and free radical scavengers. Use of radical scavengers in compositions intended for radical polymerization is counterintuitive, as these radical scavengers can directly interfere with radical polymerization processes. Surprisingly, the inventor has found that incorporation of a radical scavenger into a separator composition can permit sterilization via ionizing or radical-generating radiation of a separator composition that includes a polymerizable compound susceptible to radical polymerization without inducing significant polymerization, while not substantially interfering with later crosslinking or polymerization of such a polymerizable compound using a free radical generating photoinitiator. This advantageously permits sterilization of separation tubes containing such separator compositions by known and well established technologies such as gamma irradiation and e-beam irradiation. In preferred embodiments of the inventive concept free radical scavengers include nitroxides, such as 4-hydroxy-TEMPO (TEMPOL), and/or thiazines, such as phenothiazine. Such free radical scavengers may be present in concentrations that permit sterilization by radical generating radiation while permitting initialization of polymerization via radical generating photoiniation. In some embodiments of the inventive concept a free radical scavenger is present at concentrations ranging from about 0.5 mM to about 50 mM. In other embodiments of the inventive concept the free radical scavenger is present at concentrations ranging from about 1 mM to about 20 mM. In still other embodiments of the inventive concept the free radical scavenger is present in concentrations ranging from about 2 mM to about 8 mM.

As noted above, embodiments of the inventive concept include separation tubes that contain a separation compound and that may be sterilized using ionizing or radical generating radiation. This advantageously permits the use of well established sterilization techniques that may be applied effectively on a large scale. The ionizing radiation used may be from a gamma source (such as $^{60}$Co or $^{137}$Cs) or an e-beam source. In some embodiments of the inventive concept ionizing radiation is applied for sterilization purposes at between about 8 kGy and about 25 kGy. In a preferred embodiment of the inventive concept ionizing radiation is applied for sterilization purposes at equal to or greater than about 15 kGy.

One embodiment of the inventive concept is shown schematically in the drawing FIGURE. A sterilizable separator tube 100 that contains a separator composition 105 is exposed to radical generating energy source 110, that applies radical generating energy 115 (such as gamma radiation or e-beam radiation) to the sterilizable separator tube 100, resulting in a sterilized separator tube 120 containing a sterilized separator composition 125. Both the separator composition 105 and the sterilized separator composition 125 are flowable. A sample 130, for example blood, is added to the sterilized separator tube and mixed to form a mixture of the sample and the sterilized separator composition 135. Following separation of phases of the sample (for example, by centrifugation) this mixture resolves into a low density phase 140 and a high density phase 145 originating from the sample 130 and a layer of sterilized separator composition 150 that lies between the low density 140 and high density 145 phases. Subsequent exposure to a suitable energy source 155 (for example, a UV or visible light source) provides energy 160 that initiates radical polymerization within the separator composition to form a substantially solid, crosslinked composition 165 that acts as an impermeable barrier between the low density 140 and high density 145 phases. Surprisingly, it is possible to form such a barrier by radical polymerization despite the lack of significant polymerization of the non-crosslinked separator composition 105 following exposure to radical generating energy 115. Following polymerization of the separator composition the separator tube may be handled without risk of contamination between the separated phases. A phase may be easily and safely removed by decanting or aspiration from the separator tube using a pipettor or liquid handling probe without risk of contamination by the adjacent phase or risk of contamination or fouling of the pipettor/probe by the hairier material separating the phases (not shown).

As noted above, exposure of the separator composition to a suitable energy source (following sterilization, addition of sample, and fraction/phase separation) results in polymerization, causing it to harden to form a substantially solid, crosslinked composition. The separator substance is preferably formulated to harden to at least 1 on the Shore 00 hardness scale upon polymerization. In preferred embodiments of the inventive concept the separator compound hardens further to at least 10 on the Shore A hardness scale. In yet other embodiments of the inventive concept the separator compound hardens even further to at least 10 on the Shore D hardness scale. In order to facilitate the workflow of sample processing, in some embodiments of the inventive concept the time to for the separator composition to harden is less than about 30 minutes. In other embodiments of the inventive concept the time for the separator composition to harden is less than about 15 minutes. In a preferred embodiment of the inventive concept the time for the separator composition to harden is equal to or less than about 10 minutes. This rapid hardening of the separator composition advantageously supports the use of embodiments of the invention in a medical setting, where it is necessary to complete testing of critical samples as soon as possible.

As noted above, in order to localize between the separated fractions or phases the separator compound may be formulated with a density intermediate between them. For example, to achieve a desired initial density (typically between about 1.01 and 1.09), it is contemplated that the density may be adjusted by virtue of molecular composition, as well as by inclusion of appropriate filler material (e.g., silica, latex, or other inert material). For example, to formulate a separator compound of the inventive concept polymerizable polymer(s), radical scavenger(s), and polymerization intiator(s) may be blended to form a base mixture.

This base mixture may be stored or incubated for a period of time prior to the addition of a filler material. Filler material (for example, silica) may then be blended into the base mixture in one or more fractions to generate a density-adjusted separator composition that may subsequently be filled into separator tubes. In some embodiments of the inventive concept additional clarification steps may be performed. For example, the base mixture may be clarified prior to the addition of filler material and/or the density-adjusted separation compound may be clarified. Clarification may be performed by (for example) settling and decanting, centrifugation, filtration, or other suitable techniques. In still other embodiments of the inventive concept additional heating steps may be performed. For example, the base mixture may be heated prior to the addition of filler material, the density-adjusted separation compound may be heated, and a separator tube containing a separation compound may be heated following sterilization. In such heating steps the temperature of the materials may be brought up to between about 30° C. and about 95° C. In other embodiments of the inventive concept the temperature of the materials may be brought up to between about 40° C. and about 90° C.

It is further contemplated that a separator tube of the inventive concept may include a plurality of separator compositions characterized by different densities. In such an embodiment, separation in a device such as a centrifuge may generate three or more fractions from the fluid sample, the interface between each pair of fractions characterized by the presence of a separator composition having a density intermediate to that of the adjacent fractions. In such an embodiment of the inventive concept the separator composition may include distinct polymerization initiators, thereby permitting selective polymerization and hardening of the barriers between the fractions.

Although illustrated in the drawing FIGURE as a tube with an open end and a closed end, other configurations for the separator tube are contemplated. In some embodiments of the inventive concept the separator tube is an open ended tube in which the closed end is essentially hemispherical. In other embodiments of the inventive concept the separator tube includes one or more devices, such as a valve assembly, that may be utilized to access the interior of the separator tube to add or remove materials. For example, a separator tube may have a closed end and an end that includes a valve assembly, where the valve assembly permits controlled removal of a sample phase or fraction. Alternatively, a separator tube may have multiple valve assemblies (for example, one at each terminus) that permit controlled removal of multiple sample phases or fractions. It should be noted that the generation of a substantially solid, crosslinked barrier between the sample phases advantageously supports a variety of separation tube configurations by, for example, permitting inversion of a separation tube to simplify direct access to higher density sample phases, if desired. Alternatively, following removal of a low density sample phase, a substantially solid, crosslinked barrier may be pierced using a suitable pipettor or probe in order to access a higher density sample phase without contamination or fouling of the pipettor/probe.

Separator tubes may be composed of any material suitable to contain the sample and permit transmission of radical generating energy used for sterilization and energy used to initiate polymerization and crosslinking of the separator composition. Suitable materials should not interfere with subsequent analyses and may be biocompatible, and include (but are not limited to) glass and polymeric compositions such as polycarbonate, polyurethane, polyamides, polystyrene, polyethylene, polypropylene, polyacrylates, fluoropolymers, and/or combinations thereof. In a preferred embodiment, the separator tube is a blood collection tube, similar to a VACUTAINER™ tube (BD, Franklin Lakes, N.J. USA 07417), and is composed of a material (for example, glass or polycarbonate) that is both compatible with blood and does not interfere with the results of assays carried out upon blood or blood fractions stored therein. In some embodiments separator tubes may contain additional materials that interact with the sample. For example, a separator tube may contain a sample stabilizer, an antimicrobial agent, a cryoprotectant, an anticoagulant, an enzyme inhibitor, and/or reagents that are utilized in subsequent assays. Examples of cryprotectants include (but are not limited to) glycols, DMSO, MPD, sucrose, trehalose, and/or antifreeze proteins. Examples of anticoagulants include (but are not limited to) chelating agents (such as EDTA, ascorbate, citrate, and oxalate), heparin, and/or heparin derivatives.

In some embodiments of the inventive concept separator tubes may include additional features that aid in sample collection and storage. For example, a separator tube of the inventive concept may include an elastomeric cap or plug that serves to retain a partial vacuum within the separator tube that aids in sample collection while also preventing environmental contamination Separator tubes may include indicia, that serve to identify the contents of the separator tube, the presence of additional materials (for example, anticoagulants), and/or identifiers unique to the sample. Examples of such indicia include (but are not limited to) color coded elastomeric caps or plugs, alphanumeric or color coded tags, barcodes, RFID chips, and magnetic and/or electronic memory devices. Such indicia may advantageously serve to facilitate storage and processing of samples (or fractions thereof) held within such a separator tube and permit tracking of samples and results.

Another embodiment of the inventive concept is a kit that includes a separator tube containing a separator composition. This kit may include one or more sterilized separator tube(s) containing separator composition, provided in a sealed enclosure. Suitable enclosures include, but are not limited to, boxes, covered trays, and envelopes. Alternatively, such a kit may include one or more sterilized separator tube(s) that contain a separator composition and additional materials that may be utilized in collection of a sample. Examples of such additional materials include, but are not limited to, a protective glove, a sterile wipe, an alcohol preparative pad, a tourniquet, a phlebotomy needle, and/or a bandage.

Although particular reference has been made to the utility of the invention in the field of blood separation and analysis, it should be appreciated that embodiments of the inventive concept may be applied to a wide variety of fluids and fluid suspensions. Such fluids and/or suspensions may include macerated tissue, cell or tissue culture suspensions, fecal suspensions, seminal fluid, nucleic acid/protein isolation mixtures, organic synthesis mixtures, or any mixture where contamination between separable phases or fractions is of concern.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sterilizable separator tube comprising:
a separator composition disposed within the separator tube, the separator composition having a density of between 1.01-1.09 g/cm³ and comprising a plurality of polymerizable compounds, a radical scavenger, and a polymerization initiator, and wherein the separator composition is flowable;
wherein the radical scavenger is present in an amount effective to prevent substantial polymerization of the polymerizable compounds upon exposure of at least a portion of the separator tube to radical-generating radiation in a dosage effective for sterilization; and
wherein the polymerization initiator is present in an amount effective such that the separator composition will form a solid crosslinked composition having a hardness of at least 1 on the Shore 00 hardness scale through polymerization of the polymerizable compounds upon exposure of at least a portion of the separator tube to irradiation by an energy source for a period of less than ten minutes.

2. The separator tube of claim 1, wherein the energy source is a light source emitting ultraviolet light.

3. The separator tube of claim 1, wherein the polymerization initiator is a radical photoinitiator.

4. The separator tube of claim 1, wherein the radical scavenger is selected from the group consisting of an antioxidant, a radioprotective, a free radical inhibitor, a free radical interceptor, and a free radical scavenger.

5. The separator tube of claim 1, further comprising a radical scavenging stabilizer.

6. The separator tube of claim 1, wherein the plurality of polymerizable compounds comprise a mixture of an aliphatic urethane diacrylate and an aliphatic acrylate.

7. A method for separating phases of a sample in a separator tube, comprising:
providing a separator tube containing a flowable separator composition having a density of between 1.01-1.09 g/cm³ and comprising a plurality of polymerizable compounds, a radical scavenger, and a polymerization initiator;
irradiating the separator tube with ionizing radiation to thereby generate radicals in an amount effective for sterilization while scavenging at least some of the radicals with a radical scavenger to prevent substantial polymerization due to the step of irradiating the separator tube;
mixing a sample with the separator composition in the separator tube;
centrifuging the separator tube, thereby separating a low density phase of the sample from a high density phase of the sample such that at least a portion of the separator composition localizes between the low density phase and the high density phase;
irradiating at least a portion of the separator tube with at least one of UV light and visible light to initiate radical polymerization of the separator composition to thereby form a solid crosslinked composition having a hardness of at least 1 on the Shore 00 hardness scale between the low density phase and the high density phase; and
wherein the separator composition is formulated to form the solid crosslinked composition having the hardness of at least 1 on the Shore 00 hardness scale upon exposure to the at least one of the UV light and the visible light for a period of less than ten minutes.

8. The method of claim 7, wherein irradiation of the separator tube occurs within a centrifuge.

9. The method of claim 7, wherein the radical scavenger is selected from the group consisting of an antioxidant, a radioprotective, a free radical inhibitor, a free radical interceptor, and a free radical scavenger.

10. The method of claim 7, wherein the step of irradiating is performed with gamma irradiation or e-beam irradiation at a dosage of at least 15 kGy.

11. The method of claim 7, wherein the radical scavenger is present in a concentration of between 2 mM and 8 mM.

12. The method of claim 10, wherein the separator composition comprises a mixture of an aliphatic urethane diacrylate and an aliphatic acrylate.

13. A method of preparing a separator composition for use in a separator tube, comprising:
blending a plurality of polymerizable compounds, a radical scavenger, and a radical photoinitiator to form a base mixture;
blending a density filler into the base mixture to form a flowable density-adjusted separator composition having a density of between 1.01-1.09 g/cm³, and filling the density-adjusted separator composition into a separator tube;
irradiating the density-adjusted separator composition and the tube with a radical generating energy source for a time sufficient to sterilize the density-adjusted separator composition and the tube; and
wherein the radical scavenger is present (a) in an amount effective to scavenge radicals generated by the step of irradiating to thereby prevent substantial polymerization of the polymerizable compounds, and (b) in an amount effective such that the density-adjusted separator composition will form a solid crosslinked composition having a hardness of at least 1 on the Shore 00 hardness scale through polymerization of the polymerizable compounds upon activation of the radical photoinitiator via exposure to a suitable energy source for a period of less than ten minutes.

14. The method of claim 13, further comprising at least one step selected from the group consisting of incubating the base mixture for a predetermined period, further mixing the base mixture, and clarifying the base mixture prior to the step of blending the density filler into the base mixture.

15. The method of claim 14, further comprising a step of incubating the density-adjusted separator composition after the step of irradiating at a temperature between 40° C. and 90° C.

16. The method of claim 13, wherein the step of irradiating is performed using gamma radiation or e-beam radiation.

17. The method of claim 16, wherein activation of the radical photoinitiator comprises exposure of the radical photoinitiator to at least one of a UV light source and a VIS light source.

* * * * *

UNITED STATES PATENT AND TRADEMARK OFFICE
CERTIFICATE OF CORRECTION

PATENT NO. : 9,669,405 B2
APPLICATION NO. : 13/656926
DATED : June 6, 2017
INVENTOR(S) : Jane F. Emerson et al.

Page 1 of 1

It is certified that error appears in the above-identified patent and that said Letters Patent is hereby corrected as shown below:

On the Title Page

Item (71) please add applicant:
University of Maryland, College Park
College Park, Maryland (US)

Item (73) please add assignee:
University of Maryland, College Park
College Park, Maryland (US)

Signed and Sealed this
Sixteenth Day of October, 2018

Andrei Iancu
*Director of the United States Patent and Trademark Office*